United States Patent [19]

Liang et al.

[11] 4,013,685
[45] Mar. 22, 1977

[54] PROCESS FOR THE MANUFACTURE OF N(MERCAPTOMETHYL) PHTHALIMIDE S-(O,O-DIMETHYL PHOSPHORODITHIOATE

[75] Inventors: Shen Fu Liang, El Cerrito; Richard Alan Zeleny, Lafayette, both of Calif.

[73] Assignee: Stauffer Chemical Company, Westport, Conn.

[22] Filed: Mar. 10, 1975

[21] Appl. No.: 557,002

[52] U.S. Cl. .................. 260/326 E; 260/326 HL
[51] Int. Cl.² .......................... C07D 209/34
[58] Field of Search ............ 260/326 E, 326 HL

[56] References Cited

UNITED STATES PATENTS 2,767,194  10/1956  Fancher ................. 260/326 E

*Primary Examiner*—Dolph H. Torrence
*Attorney, Agent, or Firm*—Michael J. Bradley

[57] ABSTRACT

Disclosed herein is a novel process for the manufacture of N(mercaptomethyl) phthalimide S-(O,O-dimethyl phosphorodithioate) wherein increased production in a series of given size reaction vessels is achieved, which process comprises operating at a higher temperature and at a higher product-to-solvent ratio than hereinbefore practiced.

12 Claims, No Drawings

PROCESS FOR THE MANUFACTURE OF N(MERCAPTOMETHYL) PHTHALIMIDE S-(O,O-DIMETHYL PHOSPHORODITHIOATE)

SUMMARY OF THE INVENTION

This invention relates to a novel process for the manufacture of N(mercaptomethyl) phthalimide S-(O,O-dimethyl phosphorodithioate), hereinafter referred to as the phosphorodithioate ester. More specifically, this invention relates to an improvement in the process for the manufacture of the phosphorodithioate ester. The improvement in the production per batch of the phosphorodithioate ester is achieved with no increase in batch cycle time period. Also, the solvent requirement per pound of the phosphorodithioate ester and thus the solvent stripping load in the product purification is reduced.

BACKGROUND OF THE INVENTION

Heretofore, N(mercaptomethyl) phthalimide S-(O,O-dimethyl phosphorodithioate), see U.S. Pat. No. 2,767,194, was produced in a batch process by reaction between N-chloromethyl phthalimide, hereinafter referred to as CMP, and sodium O,O-dimethyl dithiophosphate, hereinafter referred to as dithioacid salt, as follows:

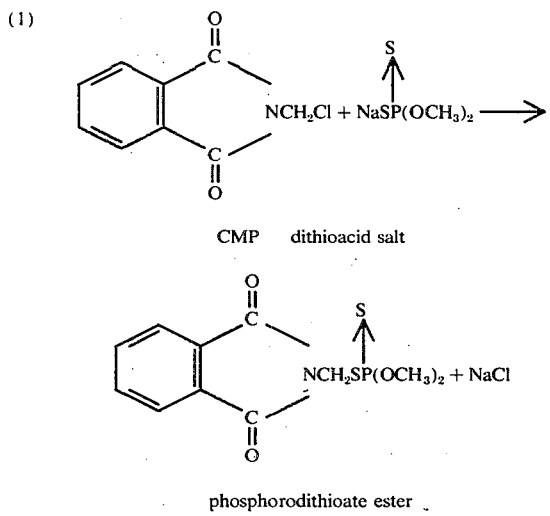

The CMP in the above reaction is formed by reaction between N-hydroxymethyl phthalimide, hereinafter referred to as HMP, and hydrochloric acid, as follows:

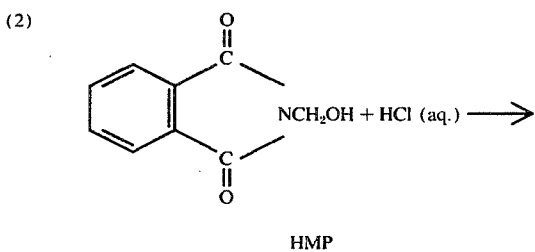

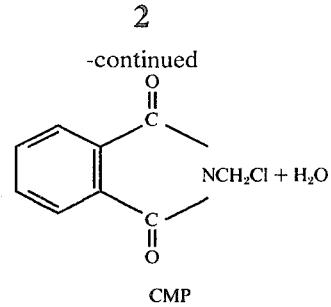

Reactions (1) and (2) are carried out in a batch process. Reaction (2) is carried out in a first reactor. The CMP produced is transferred to a second reactor where Reaction (1) is carried out.

The HMP is supplied to the first reactor in the form of a wet filter cake. The moisture in the filter cake reduces the strength of the aqueous HCl. The acid strength is fortified by the addition of anhydrous HCl, bubbled through the reaction mixture. The reaction occurs in the presence of an organic solvent such as benzene in an amount sufficient to dissolve the CMP produced in the reactor. The CMP-containing organic phase is then separated from the aqueous phase and transferred to the second reactor where it reacts with the dithioacid salt to form the phosphorodithioate ester. The product of the reaction which occurs in the second reactor is a two-phase mixture containing the phosphorodithioate ester in the lighter organic phase and sodium chloride and other aqueous wastes in the heavier aqueous phase. The phosphorodithioate ester is obtained from this mixture by phase separation followed by caustic and water washes and solvent stripping.

The procedure for the above-described process is as follows:

1. The first reactor is charged with wet HMP cake.
2. 35% aqueous HCl is added at a quantity of about 50 gallons per lb - mole of HMP.
3. Benzene is added at a quantity of about 130 gallons per lb - mole of HMP.
4. Anhydrous HCl is bubbled through the reaction mixture at a rate of from about 15 to about 25 lb per hour per lb - mole HMP charged in Step (1). As the HCl is bubbled through the mixture, the temperature is maintained at 45° C by the application of cooling water. The reaction is monitored by checking the acid strength which rises at the completion of the reaction when HMP is no longer present to consume the HCl.
5. At the completion of the reaction, the aqueous HCl phase is removed.
6. The benzene solution of CMP is pumped together with the dithioacid salt to the second reactor where the reaction to form the phosphorodithioate ester occurs. The reaction is conducted at about 70° C and about atmospheric pressure.
7. The contents of the second reactor are phase separated, the product phase is washed with caustic and water, and the solvent is stripped from the product.

BRIEF DESCRIPTION OF THE INVENTION

It has been discovered that by the use of hereinafter disclosed process for the production of the phosphorodithioate ester, which process is the process of the invention as hereinafter described, two advantages are obtained, namely:

1. The production capacities of both reactors can be increased with no change in the size of either vessel and with no increase in the overall batch cycle time, and
2. The solvent stripping load and loss per unit of product in the purification section can be reduced, conserving heat energy.

By virtue of advantage (1) above, the overall batch size can be increased by 60 to 100% over that of the previous process when the latter is operated at capacity. This advantage also offers a benefit to the design of new plants for the process, since smaller reaction vessels can be employed to achieve a production capacity that under the previous process would require larger vessels.

Stating advantage (2) more specifically, the solvent per pound of product as well as the stripping load in the purification section of the process can be reduced to about 70% of that of the previous process. Both advantages (1) and (2) are achieved at no expense with respect to either yield or purity of the product.

The process of the invention is a process for the production of N(mercaptomethyl) phthalimide S-(O,O-dimethyl phosphorodithioate in which HMP and aqueous HCl are reacted to form CMP, in a novel reaction designed to increase CMP production. This reaction is conducted in the presence of an organic solvent in the amount of 45 to 80 gallons of said solvent per lb-mole HMP at a temperature of 45° to 75° C and a pressure of 0 psig to 50 psig while in intimate contact with anhydrous HCl. The anhydrous HCl is bubbled through the mixture at a rate of 15 to 65 pounds HCl per hour per lb-mole HMP until the completion of the reaction occurs as detected by a rise in pressure in the reaction vessel. A further improvement in production of phosphorodithioate ester can be achieved by transferring the organic phase containing the CMP to the second reactor and reacting it with dithioacid salt in a molar quantity equal to from 1.1 to 1.5 times the molar quantity of the HMP originally used, to form the phosphorodithioate ester, such reaction being conducted at a temperature of 45° to 70° C and a pressure of 0 psig to 10 psig. An additional quantity of organic solvent is added before the reaction in the second reactor such that the total amount of organic solvent present corresponds to 80 to 130 gallons of organic solvent per lb-mole of the HMP originally used. The phosphorodithioate ester, which is contained in its entirety in the organic phase of the resulting two-phase mixture in the second reactor is recovered.

DETAILED DESCRIPTION OF THE INVENTION

The process of the invention is distinguished from the process described in the Background of the Invention above by a series of four improvements as hereinafter described. It is these improvements of the process which comprise the novelty of the invention and which produce the highly desirable results listed above.

The first improvement concerns the relative amounts of organic solvent and HMP charged to the first reactor prior to the reaction to form CMP (Reaction (2) above). The relative amount of organic solvent charged to the vessel prior to the reaction is reduced to from about 45 to about 80 gallons of organic solvent per lb-mole of HMP, or preferably to from about 50 to about 70 gallons of organic solvent per lb-mole of HMP. The actual volume of 35 to 40 wt. % aqueous HCl remains unchanged. By virtue of the lesser amount of organic solvent relative to HMP, the actual amount of HMP charged can be increased by up to about 100%, while still producing a total reaction mixture volume equal to or less than that of the previous process. The volume of 35 to 40 wt. % acid relative to HMP then becomes from about 25 to about 50 gallons of the acid solution per lb-mole of HMP.

In the second improvement of the process, the reaction to form CMP is conducted at an elevated temperature ranging from about 45° to about 75° C and at a pressure of from about 0 psig to about 50 psig, or preferably from about 0 psig to about 20 psig. The temperature selected from the above temperature range is equal to or higher than the temperature at which the CMP produced by the reaction will dissolve in the amount of organic solvent present. The pressure selected from the above pressure range varies as the reaction proceeds and is dependent upon the degree of completion of the reaction. As anhydrous HCl is bubbled through the reaction mixture to maintain the concentration of HCl in the aqueous phase at from 35 to 40 wt. %, the reaction is conducted preferably at close to ambient pressure until the time near the completion of the reaction when the HCl fumes begin to accumulate as both the concentration of CMp and the reaction driving force decrease. Due to the higher reaction temperature of the process of the invention over that of the normal process, the pressure rise which accompanies the accumulation of HCl fumes near the completion of the reaction is faster and more pronounced than in the previous process. The reaction is monitored by checking for this pressure rise, and it is no longer necessary to check the acid strength to determine when the reaction is completed. When the pressure rises, the feed of anhydrous HCl is discontinued. The pressure may be allowed to rise as high as 50 psig before this is done, but it is preferred that the HCl feed be discontinued when the pressure reaches about 20 psig or less.

In the third improvement of the process, the rate of addition of anhydrous HCl is increased to from about 15 to about 64 lb HCl per hour per lb-mole of HMP originally charged, or preferably to from about 45 to about 65 lb HCl per hour per lb-mole of said HMP. The heat of solution generated by the dissolving of the HCl in the reaction mixture is used to heat the contents of the first reactor or the desired reaction temperature. Additional heat may be added in the form of sensible heat to increase the rate of temperature rise in the reactor is desired, but such additional heat is not normally required. Once the desired temperature is reached, the temperature level may be maintained by the application of cooling water.

Organic solvents useful in the present invention include benzene, toluene, 1,2-dichloroethane and similar non-polar solvents.

These first three improvements provide a dramatic increase in production of HMP over prior processes.

A further improvement in production of the phosphorodithioate ester is achieved by a fourth improvement as hereinafter stated. The fourth improvement of the process is the introduction of a second charge of organic solvent in addition to the amount which is originally charged to the first reactor. The second charge of organic solvent can be added to the contents of the first reactor immediately after the removal of the aqueous HCl phase following the reaction to form CMP. The CMP-containing organic phase whose volume has been increased by the second charge of organic solvent is then mixed with an aqueous solution of a molar quantity of the dithioacid salt equal to from 110 to about 150%, or preferably from about 110 to about 130% of the molar quantity of HMP originally used. In this mixture, the CMP is reacted with the dithioacid salt at a temperature of from about 45° to about 70° C and at a pressure ranging from ambient to about 10 psig, to form the phosphorodithioate ester in an aqueous-organic mixture. The second charge of organic solvent can alternatively be added at any point or time subsequent to the removal of the aqueous HCl phase from the first reactor and prior to the reaction in the second reactor. The second organic solvent charge prevents emulsion formation or breaks any emulsion formed in the second reactor. Separation of the organic phase with the phosphorodithioate ester dissolved therein from the aqueous-organic mixture can then be carried out with no greater a degree of difficulty than in the previous process. Such separation is effected in any manner known in the art such as allowing the phases to settle followed by decantation of the heavier phase. The phosphorodithioate ester can then be recovered from the organic phase by methods known in the art such as vacuum distillation or inert gas stripping. The quantity of organic solvent in the second charge is such that the total of both the first and second organic solvent charges represents from about 80 to about 130 gallons of organic solvent per lb - mole of HMP originally charged to the first reactor. If the second organic solvent charge brings the total up to 130 gallons of organic solvent per lb - mole of HMP, the stripping advantage of the invention will be lost. At amounts less than 130 gallons of organic solvent per lb - mole of HMP, not only is a stripping advantage gained, but the quantity of equivalent CMP that the second reactor can hold is increased over that of the normal process.

The following example serves to illustrate further the process of the invention but it is not to be construed as limiting the invention in any manner whatsoever.

EXAMPLE

In this example, a comparison is made between utilization of the previous process and utilization of the process of the invention in a typical plant. A vessel corresponding to the first reactor and having a capacity of 2000 gal is charged with the amounts of materials listed in Table I under both the previous process and the process of the invention. The conditions under which each of the two processes was carried out are listed in Table II.

TABLE I

| Charge List for First Reactor | Previous Process | Improved Process |
|---|---|---|
| Aqueous 35% HCl, gal. | 500 | 500 |
| HMP, lb. - moles | 10.5 | 16.5 |
| Benzene added prior to chlorination, gal. | 1350 | 1025 |
| Benzene added after removal of aqueous HCl, gal. | 0 | 510 |
| Total benzene, gal. | 1350 | 1535 |

TABLE II

| Reaction Conditions in First Reactor | Previous Process | Improved Process |
|---|---|---|
| First Reactor | | |
| Reactor capacity, gal. | 2000 | 2000 |
| Temperature, °C | 45 | 65 |
| Reaction time, hr. | 3.5 | 1.5 |
| Rate of addition of anhydrous HCl, lb./hr. | 230–300 | 960 |
| First and Second Reactors | | |
| Overall batch cycle time, hr. | 8.0 | 7.5 |

In the example of the previous process, the first reactor is operated at capacity. In the example of the improved process, 57% more HMP is charged to the first reactor over the amount charged in the normal process. In spite of the higher amount of HMP in the improved process, the amount of benzene charged prior to chlorination is less, and the first reactor is operated at only 87% of its volumetric capacity.

In the example of the improved process, the second benzene charge is added to the first reactor after the removal of the aqueous HCl, bringing the total amount of benzene used to an amount higher than the benzene charge in the previous process. The higher total, however, only amounts to 93 gal/lb - mole HMP as compared to 128 gal/lb - mole HMP in the example of the previous process. Thus the stripping load per pound of product in the purification section following the second reactor is about 72% of that of the example of the previous process.

As Table II indicates, the reaction time in the example of the improved process is considerably shorter than that in the example of the previous process. Most of this time advantage is lost in the overall batch cycle time because of the increased time required to handle the greater amounts of HMP and CMP per batch in the improved process. Thus, the overall batch cycle time is approximately the same under both processes.

Following the phase separation in the second reactor in both the previous and improved processes, the product-containing organic phase is first washed with a 10% caustic solution, then with water. The solvent in the organic phase is then stripped from the product. The product yield in each case is approximately 73%, and the purity of the phosphorodithioate ester produced is approximately 95% in each case. This similarity in both yield and purity occurs despite the use of a higher reaction temperature where normally one would expect a higher amount of by-product.

What is claimed is:
1. A process for the production of N-chloromethyl phthalimide, comprising the steps of:
 a. Forming a mixture of N-hydroxymethyl phthalimide, an organic solvent in the amount of 45 to 80 gallons of said solvent per pound-mole of said N-hydroxymethyl phthalimide, and 25 to 50 gallons of an aqueous solution of 35 to 40 wt.% HCl per pound-mole of said N-hydroxymethyl phthalimide;
 b. reacting said mixture at a temperature of from about 45° to about 75° C at a pressure of from about 0 psig to about 50 psig while intimately contacting said reacting mixture with anhydrous HCl at a rate of from approximately 15 to approximately 65 pounds HCl per hour per pound-mole of N-hydroxymethyl phthalimide used to form the mixture in step (a), to maintain the concentration of said aqueous HCl at 35 to 40 wt.%, to form N-chloromethyl phthalimide in an aqueous-organic mixture;

c. separating the organic phase having the N-chloromethyl phthalimide dissolved therein from said aqueous-organic mixture; and d. recovering said N-chloromethyl phthalimide from said organic phase.

2. A process for the production of N(mercaptomethyl) phthalimide S-(O,O-dimethyl phosphorodithioate), comprising the steps of:

a. Forming a mixture of N-hydroxymethyl phthalimide, an organic solvent in the amount of 45 to 80 gallons of said solvent per pound-mole of said N-hydroxymethyl phthalimide, and 25 to 50 gallons of an aqueous solution of 35 to 40 wt.% HCl per pound-mole of said N-hydroxymethyl phthalimide;

b. reacting said mixture at a temperature of from about 45° to about 75° C at a pressure of from about 0 psig to about 50 psig which intimately contacting said reacting mixture with anhydrous HCl at a rate of from approximately 15 to approximately 65 pounds HCl per hour per pound-mole of N-hydroxymethyl phthalimide used to form the mixture in step (a), to maintain the concentration of said aqueous HCl at 35 to 40 wt.%, to form N-chloromethyl phthalimide in a first aqueous-organic mixture;

c. separating the organic phase having the N-chloromethyl phthalimide dissolved therein from said first aqueous-organic mixture;

d. forming a second mixture of said separated organic phase having the N-chloromethyl phthalimide dissolved therein from step (c) and an additional quantity of organic solvent such that the total of the quantities of said solvent added in this step and in step (a) amount to 80 to 130 gallons of said solvent per pound-mole N-hydroxymethyl phthalimide used to form the mixture in step (a), a sodium O,O-dimethyl dithiophosphate in a molar quantity equal to from 110 to about 150% of the molar quantity of N-hydroxymethyl phthalimide used to form the mixture in step (a);

e. reacting said second mixture at a temperature of from about 45° to about 70° C at a pressure ranging from ambient to about 10 psig, to form N(mercaptomethyl) phthalimide S-(O,O-dimethyl phosphorodithioate) in a second aqueous-organic mixture;

f. separating the organic phase having the N(mercaptomethyl) phthalimide S-(O,O-dimethyl phosphorodithioate) dissolved therein from said second aqueous-organic mixture; and g. recovering the N(mercaptomethyl) phthalimide S-(O,O-dimethyl) phosphorodithioate) from said organic phase.

3. A process according to claim 1 in which from about 50 to about 70 gallons of an organic solvent per pound-mole of said N-hydroxymethyl phthalimide is used to form the mixture of step (a).

4. A process according to claim 2 in which from about 50 to about 70 gallons of an organic solvent per pound-mole of said N-hydroxymethyl phthalimide is used to form the mixture of step (a).

5. A process according to claim 1 in which the reaction of step (b) is conducted at a pressure of from about 0 psig to about 20 psig.

6. A process according to claim 2 in which the reaction of step (b) is conducted at a pressure of from about 0 psig to about 20 psig.

7. A process according to claim 1 in which the reacting mixture of step (b) is intimately contacted with anhydrous HCl at a rate of from approximately 45 to approximately 65 pounds HCl per hour per pound-mole N-hydroxymethyl phthalimide used to form the mixture of step (a).

8. A process according to claim 2 in which the reacting mixture of step (b) is intimately contacted with anhydrous HCl at a rate of from approximately 45 pounds HCl per hour per pound-mole of N-hydroxymethyl phthalimide used to form the mixture of step (a).

9. A process according to claim 2 in which the sodium O,O-dimethyl dithiophosphate used to form the mixture of step (d) is present in a molar quantity equal to from about 110 to about 130% of the molar quantity of N-hydroxymethyl phthalimide used to form the mixture in step (a).

10. A process according to claim 2 in which the reaction of step (e) is conducted at a temperature of from about 50° to about 65° C.

11. A process according to claim 1 in which said organic solvent is benzene and from about 50 to about 70 gallons of said benzene per pound-mole of said N-hydroxymethyl phthalimide is used to form the mixture of step (a); the reaction of step (b) is conducted at a pressure of from about 0 psig to about 20 psig; and the reacting mixture of step (b) is intimately contacted with anhydrous HCl at a rate of approximately 45 to approximately 65 pounds HCl per hour per pound-mole of N-hydroxymethyl phthalimide used to form the mixture in step (a).

12. A process according to claim 2 in which said organic solvent is benzene and from about 50 to about 70 gallons of said benzene per pound-mole of said N-hydroxymethyl phthalimide is used to form the mixture of step (a); the reaction of step (b) is conducted at a pressure of from about 0 psig to about 20 psig; the reacting mixture of step (b) is intimately contacted with anhydrous HCl at a rate of approximtely 45 to approximately 65 pounds HCl per hour per pound-mole of N-hydroxymethyl phthalimide used to form the mixture in step (a); sodium O,O-dimethyl dithiophosphate equal in molar quantity to from about 110 to about 130% of the molar quantity of N-hydroxymethyl phthalimide used to form the mixture in step (a) is used to form the mixture in step (d); and the reaction of step (e) is conducted at a temperature of from about 50° to about 65° C.

* * * * *

UNITED STATES PATENT AND TRADEMARK OFFICE
CERTIFICATE OF CORRECTION

PATENT NO. : 4,013,685
DATED : March 22, 1977
INVENTOR(S) : Shen-Fu Liang et al.

It is certified that error appears in the above-identified patent and that said Letters Patent are hereby corrected as shown below:

Column 3, line 24, the words reading "(O,O-dimethyl phosphorodithioate" should read ---(O,O-dimethyl phosphorodithioate)---.

Column 4, line 25, the letters reading "CMp" should read ---CMP---.

Column 7, line 22, the word reading "which" should read ---while---.

Column 7, line 59, the words reading "S-(O,O-dimethyl phosphorodithioate)" should read ---S-(O,O-dimethyl phosphorodithioate)---.

Column 8, line 17, the word reading "mole" should read ---mole of---.

Column 8, line 21, the words reading "approximately 45" should read ---approximately 45 to approximately 65---.

Signed and Sealed this

Thirteenth Day of December 1977

[SEAL]

Attest:

RUTH C. MASON
Attesting Officer

LUTRELLE F. PARKER
Acting Commissioner of Patents and Trademarks